(12) United States Patent
Ichikawa et al.

(10) Patent No.: US 9,060,901 B2
(45) Date of Patent: Jun. 23, 2015

(54) DISPOSABLE WEARING ARTICLE

(75) Inventors: Makoto Ichikawa, Kanonji (JP);
Kenichi Sasayama, Kanonji (JP);
Kunihiko Katsuragawa, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 204 days.

(21) Appl. No.: 13/810,829

(22) PCT Filed: Aug. 31, 2011

(86) PCT No.: PCT/JP2011/004853
§ 371 (c)(1),
(2), (4) Date: Jan. 17, 2013

(87) PCT Pub. No.: WO2012/029295
PCT Pub. Date: Mar. 8, 2012

(65) Prior Publication Data
US 2013/0123735 A1 May 16, 2013

(30) Foreign Application Priority Data

Aug. 31, 2010 (JP) .................................. 2010-195117

(51) Int. Cl.
*A61F 13/15* (2006.01)
*A61F 13/49* (2006.01)
*A61F 13/496* (2006.01)
(Continued)

(52) U.S. Cl.
CPC . *A61F 13/49061* (2013.01); *A61F 2013/51322* (2013.01); *A61F 13/51464* (2013.01);
(Continued)

(58) Field of Classification Search
CPC ............... A61F 2013/51322; A61F 13/51464; A61F 13/49011; A61F 13/49061; A61F 13/49017; A61F 13/496; A61F 13/51478; A61F 2013/49028; A61F 2013/49033; A61F 2013/49038; A41B 9/001

USPC ............ 604/385.24, 385.25, 385.26, 385.27, 604/385.29, 385.3
See application file for complete search history.

(56) References Cited

U.S. PATENT DOCUMENTS

| | | | |
|---|---|---|---|
| 5,941,865 | A | 8/1999 | Otsubo et al. |
| 2005/0177125 | A1 | 8/2005 | Kondo |
| 2013/0123736 | A1* | 5/2013 | Ichikawa et al. ......... 604/385.19 |

FOREIGN PATENT DOCUMENTS

| | | |
|---|---|---|
| EP | 2067459 A1 | 6/2009 |
| EP | 2327384 A1 | 6/2011 |

(Continued)

OTHER PUBLICATIONS

International Search Report corresponding to PCT/JP2011/004853, dated Nov. 15, 2011.

(Continued)

*Primary Examiner* — Jacqueline Stephens
(74) *Attorney, Agent, or Firm* — Lowe Hauptman & Ham, LLP

(57) ABSTRACT

A diaper includes front and rear waist members and a crotch member. The front and rear waist members are respectively formed with first narrowly-spaced elastic zones, widely-spaced elastic zones and second narrowly-spaced elastic zones adjacent one to another. Front and rear ends of the crotch member are bonded to respective sides of the front and rear waist members so that the crotch member's front and rear ends may positionally correspond to the second narrowly-spaced elastic zones. Cover sheets are attached to the side of the crotch member to cover the crotch member's front and rear ends respectively. A length dimension of the cover sheet in the longitudinal direction is set to be smaller than those of the front and rear waist members and a length dimension of the cover sheet in the transverse direction is substantially equal to those of the front and rear waist members.

17 Claims, 5 Drawing Sheets

(51) Int. Cl.
*A41B 9/00* (2006.01)
*A61F 13/513* (2006.01)
*A61F 13/514* (2006.01)

(52) U.S. Cl.
CPC ..... *A61F13/49011* (2013.01); *A61F 13/49017* (2013.01); *A61F 13/496* (2013.01); *A61F 13/51478* (2013.01); *A41B 9/001* (2013.01); *A61F 2013/49028* (2013.01); *A61F 2013/49033* (2013.01); *A61F 2013/49038* (2013.01)

(56) References Cited

FOREIGN PATENT DOCUMENTS

| | | |
|---|---|---|
| JP | 4-364845 A | 12/1992 |
| JP | 6-000421 U | 1/1994 |
| JP | 7-184947 A | 7/1995 |
| JP | 9-084826 A | 3/1997 |
| JP | 2004-329238 A | 11/2004 |
| JP | 2006-061681 A | 3/2006 |
| JP | 2006-247009 A | 9/2006 |
| JP | 2009-207778 A | 9/2009 |
| JP | 2009-240695 A | 10/2009 |
| WO | 2010032581 A1 | 3/2010 |

OTHER PUBLICATIONS

Supplementary European Search Report dated Jun. 23, 2014, corresponds to European application No. 11821316.4.

* cited by examiner

DISPOSABLE WEARING ARTICLE

RELATED APPLICATIONS

The present application is a National Phase of International Application Number PCT/JP2011/004850, filed Aug. 31, 2011, and claims priority from Japanese Application No. 2010-195012,filed Aug. 31, 2010.

TECHNICAL FIELD

The present disclosure relates to disposable wearing articles and more particularly to various types of disposable wearing articles, such as disposable diapers, disposable toilet-training pants, disposable incontinent pants and disposable sanitary napkins.

BACKGROUND ART

Disposable diapers provided with elastic members extending circumferentially around the wearer's body so that the diaper may be kept in close contact with the wearer's body with desired fit are known. For example, JP 1992-364845 A (PTL 1) and JP 2006-61681 A (PTL 2) disclose pants-type diapers adapted to provide fit pressure depending on zones arranged in a longitudinal direction from a peripheral edge of a waist-opening to a crotch region.

CITATION LIST

Patent Literature

{PTL 1} JP 1992-364845 A
{PTL 2} JP 2006-61681 A

SUMMARY OF INVENTION

Technical Problem

The diaper disclosed in PTL 1 includes an inner sheet, an outer sheet and a liquid-absorbent structure sandwiched between these two sheets, wherein elastic members attached along the periphery of the waist-opening, the peripheries of the respective leg-openings and circumferentially around the front and rear waist regions respectively have tensile stresses different one from another. The diaper disclosed in PTL 2 includes a chassis and a liquid-absorbent structure wherein four regions defined by quartering the range extending from the waist-opening to the leg-openings provide different fit pressures when the diaper is put on the wearer's body.

In the diapers, in the region occupied by the liquid-absorbent structure, the elastic members are either discontinuously arranged so as to avoid overlapping the liquid-absorbent structure or continuously arranged to extend across the liquid-absorbent structure. In the latter case, the inventor(s) have recognized that the liquid-absorbent structure is pressed by the elastic members against the wearer's body, and as a consequence, there is a possibility that body waste might come in contact with the wearer's body and eventually cause the wearer to suffer from diaper rash. In the former case, the inventor(s) have recognized that there is anxiety that the tensile stress might be insufficient for proper fit of the diaper to the wearer's body and the diaper might slip down under the mass of body waste.

Solution to Problem

According to one or more embodiments of the present invention, there is provided a disposable wearing article having a longitudinal direction and a transverse direction, and including a body-facing side for facing the wearer's body, a garment-facing side for facing away from the wearer's body, a front waist region defined by a front waist member, a rear waist region defined by a rear waist member and a crotch region defined by a crotch member and extending in the longitudinal direction between the front waist region and the rear waist region. The front and rear waist members are respectively provided with a plurality of waist elastics extending in the transverse direction and spaced one from another in the longitudinal direction. The waist elastics are bonded under tension and in a contractible manner to the front and rear waist members.

The crotch member has front and rear ends which extend in the transverse direction and along which the crotch member is bonded to the respective garment-facing sides of the front and rear waist members in first bonded regions extending in the transverse direction. At least one of the front and rear waist members has a plurality of elastic zones defined in the longitudinal direction and having different tensile stresses in the transverse direction. The first bonded regions are formed in associated high elastic zones included in the plurality of elastic zones and having the highest tensile stress.

Advantageous Effects of Invention

According to one or more embodiments of the present invention, the crotch member is joined to the respective garment-facing sides of the front and rear waist members and at least one of the front and rear waist members includes a plurality of elastic zones arranged in the longitudinal direction and differentiated in the tensile stress in the transverse direction so that the first bonded region or regions are be formed in the high elastic zone or zones having the highest tensile stress. With such arrangement, the crotch member can be kept in close contact with the wearer's body in the regions in which the crotch member is joined to the front and rear waist members. In this state, the crotch member should not be excessively tightened against the wearer's body under the tensile stress of the high elastic zone or zones. This is for the reason that the crotch member is joined to the respective garment-facing sides of the front and rear waist members. Consequentially, there is no possibility that body waste might flow from the crotch member into the front and rear waist regions, eventually come in direct contact with the wearer's skin and cause the wearer to suffer from uncomfortable diaper rash.

BRIEF DESCRIPTION OF DRAWINGS

One or more embodiments of the present invention will be more fully understood and further advantages will become apparent when reference is made to the following detailed description of one or more embodiments of the invention and the accompanying drawings, in which:

In FIGS. 3 through 6, respective elastics are shown in a stretched state against contractile forces thereof.

The diaper has an imaginary longitudinal center line P-P bisecting a width dimension of the diaper in a transverse direction X and an imaginary transverse center line Q-Q bisecting a length dimension of the diaper in a longitudinal direction Y wherein the diaper is substantially symmetric about the imaginary longitudinal center line P-P.

In the accompanying drawings, reference sign will be eliminated for one of respective paired portions being symmetric as the case may be.

DESCRIPTION OF EMBODIMENTS

Figure 1:
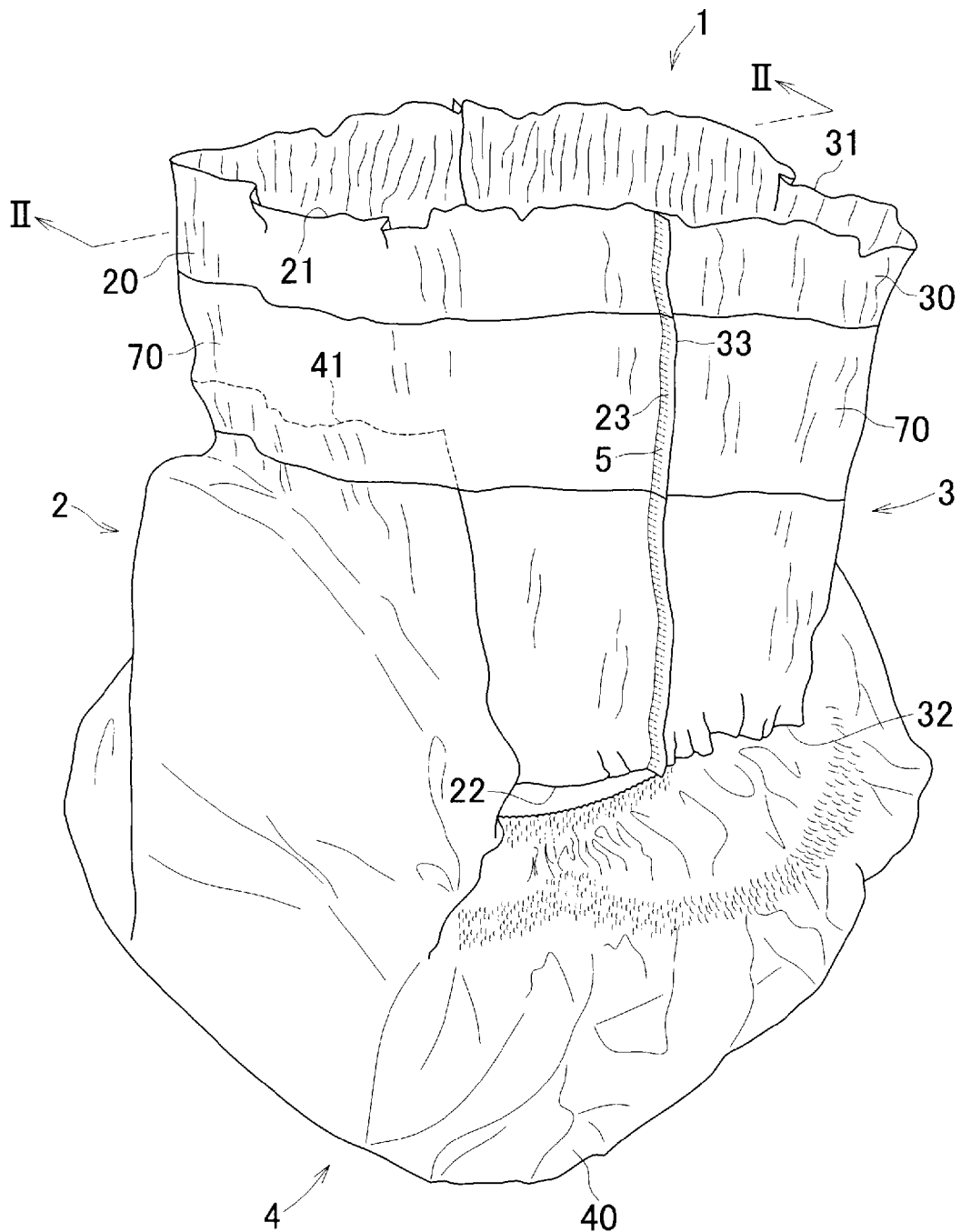
FIG. 1 is a perspective view of a disposable diaper as one example of a disposable wearing article according to an embodiment of the present invention.

Referring now to FIG. 1, a diaper 1 has a body-facing side for facing the wearer's body, a side opposite thereto (i.e., a garment-facing side for facing the wearer's garment), a front waist region 2, a rear waist region 3 and a crotch region 4 extending between the front and rear waist regions 2, 3 wherein these regions are continuous in a longitudinal direction Y. The diaper 1 includes front and rear waist members 20, 30 defining the front and rear waist regions 2, 3, respectively, and a crotch member 40 defining the crotch region 4. The front waist member 20 is contoured by outer and inner ends 21, 22 spaced from each other in the longitudinal direction Y and extending in a transverse direction X and side edges 23 spaced from each other in the transverse direction X and extending in the longitudinal direction Y. The rear waist member 30 is contoured by outer and inner ends 31, 32 spaced from each other in the longitudinal direction Y and extending in the transverse direction X and side edges 33 spaced from each other in the transverse direction X and extending in the longitudinal direction Y. The front and rear waist members 20, 30 are joined to each other at seams 5 arranged along the respective side edges 23, 33 thereof and thereby the front and rear waist members 20, 30 are maintained in an annular shape. It should be noted here that the seams 5 are defined by a plurality of, e.g., sonic-bonds arranged along the respective side edges 23, 33.

Figure 2:
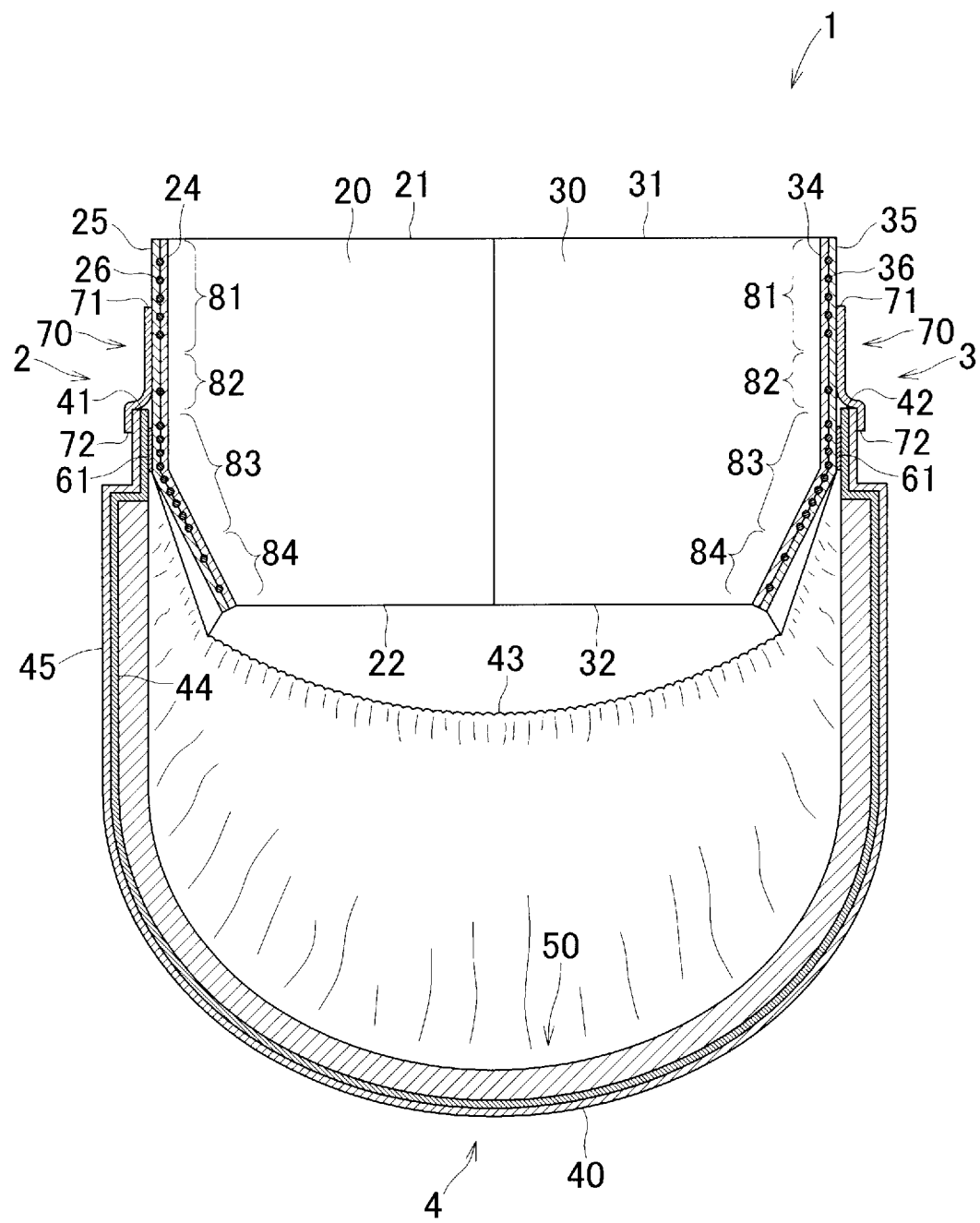
FIG. 2 is a sectional view taken along line II-II in FIG. 1.
Figure 3:
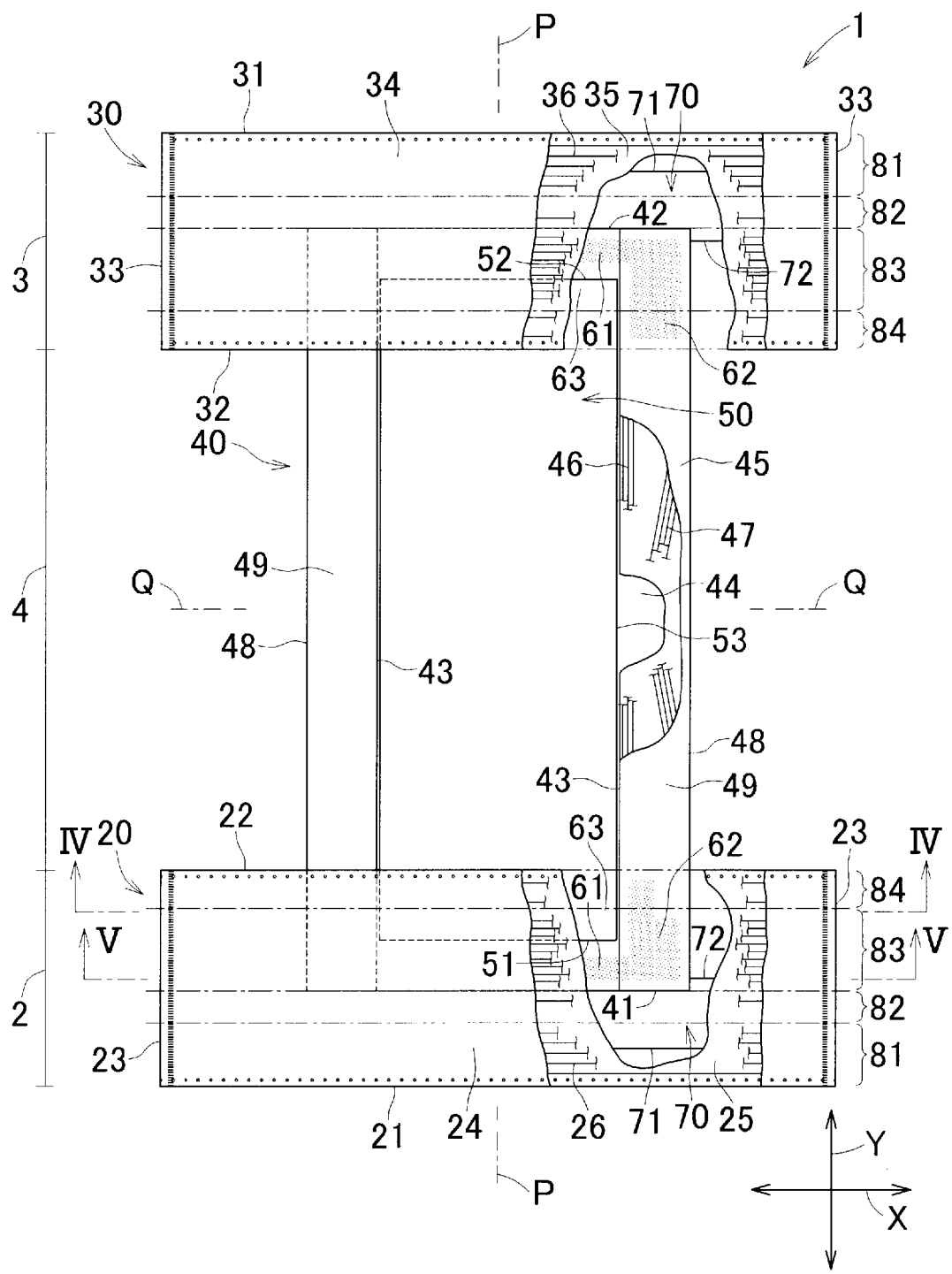
FIG. 3 is a developed plan view of the diaper as viewed from a body-facing side.

Referring to FIGS. 2 and 3, the front and rear waist members 20, 30 respectively include inner sheets 24, 34 for facing the wearer's body, outer sheets 25, 35 opposite to the respective inner sheets 24, 34, i.e., for facing away from the wearer's body, and a plurality of front and rear waist elastics 26, 36 sandwiched between these inner and outer sheets, respectively. The front and rear waist inner sheets 24, 34 and the front and rear waist outer sheets 25, 35 may be formed, for example, by fibrous nonwoven fabrics each having a mass per unit area of about 10 to about 30 g/m². The front and rear waist elastics 26, 36 respectively are spaced one from another in the longitudinal direction Y and can be attached under tension and in a contractible manner in the transverse direction X to the front and rear waist members 20, 30 so as to elasticize the front and rear waist members 20, 30 in the transverse direction X. The front and rear waist elastics 26, 36 may be implemented in the form of yarns or threads. These front and rear waist elastics 26, 36 may be bonded to at least one of the inner and outer sheets constituting each of the front and rear waist members with hot melt adhesives (not shown).

One or both of the front and rear waist members 20, 30 is/are respectively formed with a plurality of elastic zones successively arranged in the longitudinal direction so that the tensile stress thereof in the transverse direction may be different depending on positions occupied by the respective zones. According to the present embodiment, the front and rear waist members 20, 30 are respectively formed with waist elastic zones 81, low elastic zones 82, high elastic zones 83 and leg elastic zones 84 contiguously arranged from the front and rear waist members' outer ends 21, 31 to the front and rear waist members' inner ends 22, 32 in this order.

According to one preferred embodiment, five elastic yarns or threads each having fineness of about 940 dtex are attached at a pitch of approximately 8 mm to the respective waist elastic zones 81 extending inward from the outer ends 21, 31 of the front and rear waist members 20, 30 by approximately 50 mm in the longitudinal direction. A single elastic yarn having fineness of approximately 780 dtex is attached to the respective low elastic zones 82 each having a length of about 25 mm in the longitudinal direction. Nine elastic yarns or threads each having fineness of approximately 940 dtex are attached at a pitch of approximately 6 mm to the respective high elastic zones 83. Two elastic yarns or threads each having fineness of approximately 780 dtex are attached at a pitch of approximately 15 mm to the respective leg elastic zones 84.

With the aforementioned arrangement, values of the tensile stress in the respective elastic zones 81 through 84 according to the present embodiment as measured in the transverse direction is graded from the highest value to the lowest value in the order of the high elastic zones 83, the waist elastic zones 81, the leg elastic zones 84 and the low elastic zones 82.

The crotch member 40 is contoured by front and rear ends 41, 42 extending in the transverse direction X and transversely opposite side edge portions 43 extending in the longitudinal direction Y, and includes an inner sheet 44 for facing the wearer's body, an outer sheet 45 for facing the wearer's garment, and first and second crotch elastics 46, 47 respectively sandwiched between the inner and outer sheets 44, 45. The inner sheet 44 may be formed of a liquid-impervious but moisture-pervious plastic film and the outer sheet 45 may be formed of a liquid-impervious fibrous nonwoven fabric.

The side edge portions 43 of the crotch member 40 are folded inward in the transverse direction X along respective fold lines 48 extending in the longitudinal direction Y to define respective folded regions 49 in which the inner sheet 44 of the crotch member 40 faces itself. In these folded regions 49, the inner sheet 44 of the crotch member 40 are bonded to itself with hot melt adhesives or the like (not shown).

The first and second crotch elastics 46, 47 can be respectively provided in the form of two or more yarns or threads and may be attached under tension and in a contractible manner in the longitudinal direction Y to the crotch member 40 to elasticize the side edge portions 43 in the longitudinal direction Y. The first crotch elastics 46 are attached to the crotch member 40 along its transversely opposite side edge portions 43. The second crotch elastics 47 are attached to the crotch member 40 closer to the fold lines 48 than the first crotch elastics 46. Segments of the second crotch elastics 47 between the side edges 53 of the absorbent structure 50 and the fold lines 48 are curved from the fold lines 48 in the vicinities of the front and rear ends 41, 42 toward an imaginary center line Q-Q. The first and second crotch elastics 46, 47 are bonded to at least one of the inner and outer sheets 44, 45 of the crotch member 40 with hot melt adhesives or the like (not shown).

Figure 4:
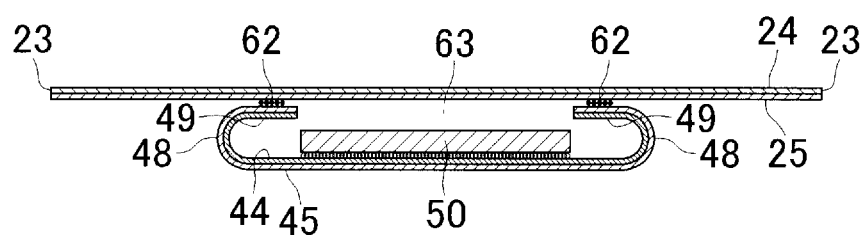
FIG. 4 is a sectional view taken along line IV-IV in FIG. 3.
Figure 5:
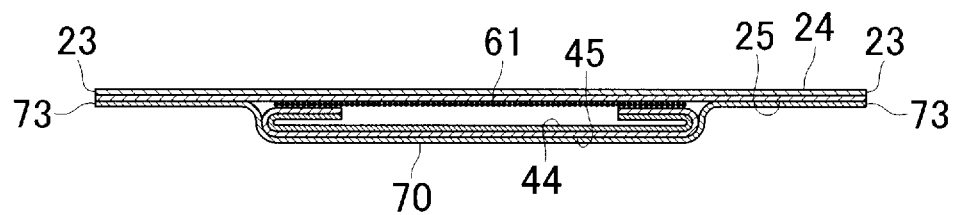
FIG. 5 is a sectional view taken along line V-V in FIG. 3.
Figure 6:
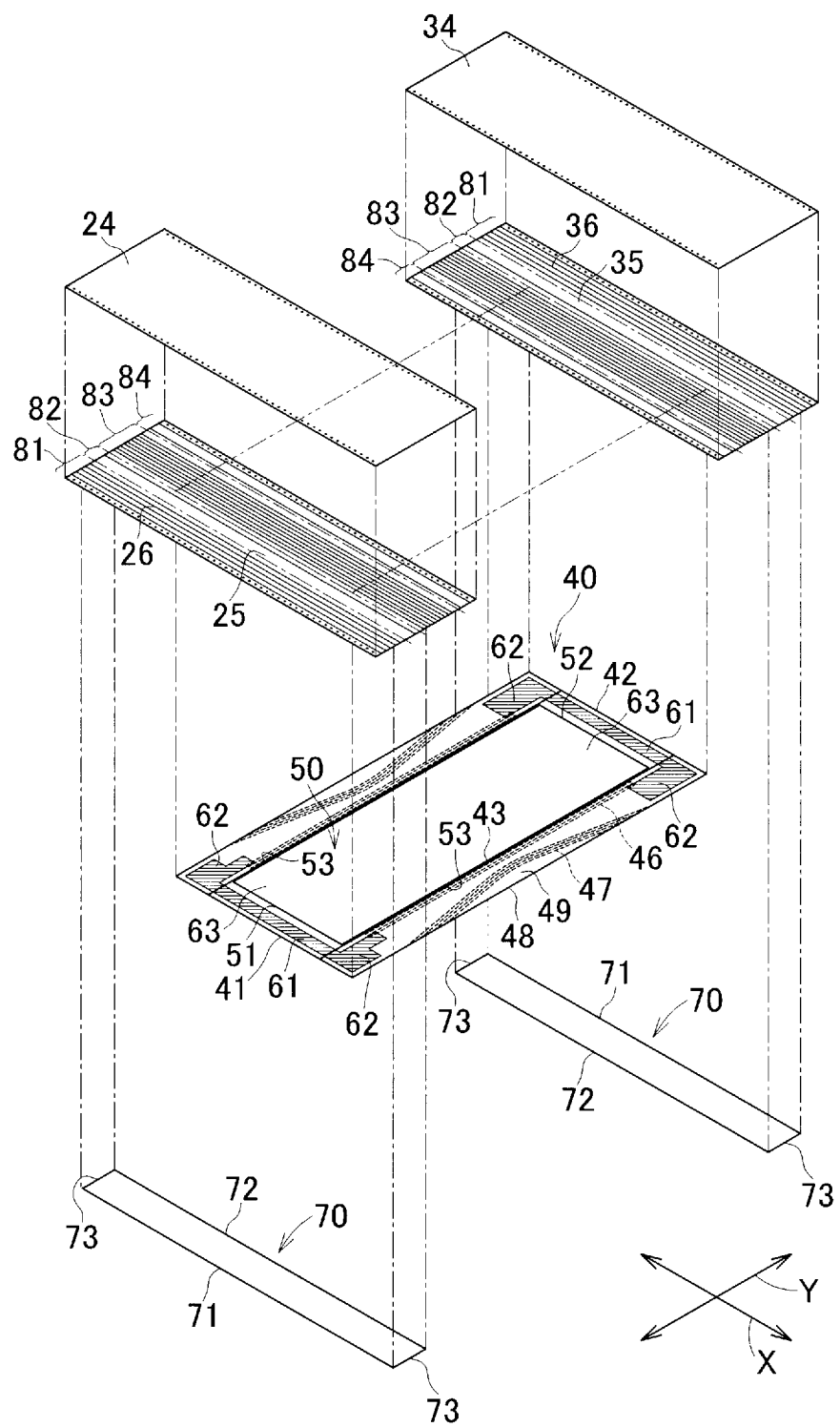
FIG. 6 is an exploded perspective view of the diaper.

A liquid-absorbent structure 50 is placed on the body-facing side of the crotch member 40. The liquid-absorbent structure 50 includes liquid-absorbent core materials, such as fluff wood pulp, super-absorbent polymer particles or a mixture thereof, and a wrapping sheet that wraps the core materials. The liquid-absorbent structure 50 is contoured by front and rear ends 51, 52 extending in the transverse direction X and transversely opposite side edges 53 thereof extending in the longitudinal direction Y. In the liquid-absorbent structure 50, front and rear ends 51, 52 lie between the front and rear ends 41, 42 of the crotch member 40 in the longitudinal direction Y, and the side edges 53 of the liquid-absorbent structure 50 lie between the fold lines 48 in the transverse direction X (See FIGS. 3 and 4).

The liquid-absorbent structure 50 is bonded to the crotch member 40 with hot melt adhesives or the like (not shown). The liquid-absorbent structure 50, which is relatively bulky, lies between the fold lines 48 as viewed in the transverse direction X and therefore the crotch region 4 does not, as a whole, become bulky due to the presence of the liquid-absorbent structure 50. The first and second crotch elastics 46, 47 are attached outboard of the liquid-absorbent structure 50 as viewed in the transverse direction X so that the side edge portions 43 of the crotch member 40 are elasticized by the crotch elastics to whereby come in close contact with the wearer's thighs and prevent body waste, such as urine, from leaking out.

The crotch member 40 is bonded at least along its front and rear ends 41, 42 to the respective garment-facing sides of the front and rear waist members 20, 30 with hot melt adhesives or the like. Specifically, between the crotch member 40 and the respective outer sheets 25, 35 of the front and rear waist members 20, 30, first bonded regions 61 extending in the transverse direction X along the front and rear ends 41, 42 of the crotch member 40, and second bonded regions 62 extending in the longitudinal direction Y outboard of both transversely opposite sides of the first bonded regions 61 as viewed in the transverse direction X are formed. More specifically, in the first bonded regions 61, the crotch member's inner sheet 44 is bonded along its front and rear ends 41, 42 to the outer sheets 25, 35 of the front and rear waist members 20, 30 and, in the second bonded regions 62, the crotch member's outer sheet 45 is bonded in its folded regions 49 to the outer sheets 25, 35 of the front and rear waist members 20, 30. Respective length dimensions of the second bonded regions 62 in the longitudinal direction Y are larger than those of the first bonded regions 61. Between these first and second bonded regions 61, 62, non-bonded regions 63 not being coated with adhesives or the like are defined. The non-bonded regions 63 are defined substantially in central areas in the transverse direction X and these first and second bonded regions 61, 62 cooperate with the non-bonded regions 63 to define concavities or pockets that are opened toward the crotch region 4.

In the diaper according to the present embodiment, the crotch member 40 is bonded to the respective garment-facing sides of the front and rear waist members 20, 30.

In consequence, body waste, such as urine, would not move to the respective body-facing sides of the front and rear waist members 20, 30 even if body waste flows on the crotch member 40 in the longitudinal direction Y toward the front and rear waist members 20, 30. In this way, it is possible to protect the wearer against suffering from diaper rash due to direct contact of body waste with the wearer's skin. The crotch member 40 is bonded to the front and rear waist members 30, 40 in the first bonded regions 61 and the second bonded regions 62, respectively, and the pockets opening toward the crotch region 4 are defined by the non-bonded regions 63. More specifically, the vicinity of the transversely opposite side edge portions 43 of the crotch member 40 defining the respective non-bonded regions 63, the vicinity of the respective inner ends 22, 32 of the front and rear waist members 20, 30 extending between the transversely opposite side edge portions 43 of the crotch member 40 and the vicinity of the front and rear ends 41, 42 of the crotch member 40 cooperate together to define the pockets. Each pocket defined in this manner is arranged to contain body waste moving along the crotch member 40 in the longitudinal direction Y and to prevent such body waste from flowing back toward the front and rear waist members 20, 30.

The first bonded regions 61 are respectively formed in the high elastic zones 83 of the front and rear waist members 20, 30. In consequence, the tensile stress of the high elastic zones 83 in the transverse direction serves to support the joint between the crotch member 40 and the front and rear waist members 20, 30 in the first bonded regions 61 on its proper position. With such arrangement, even when the mass of the crotch region increases due to body waste discharged by the diaper wearer, the front and rear waist members 20, 30 would not slip down along the wearer's body under the increased mass of the crotch region.

According to the present embodiment, the high elastic zones 83 extend in the longitudinal direction in a range between about 75 mm and about 140 mm from the respective front and rear waist members' outer ends 21, 31. Assuming that the diaper 1 according to this embodiment is put on an adult wearer's body, such a range will nearly correspond to the wearer's ilium. Even if a relatively high tensile stress is exerted on this region of the wearer, such tensile stress would not make the wearer uncomfortable.

Each of the low elastic zones 82 allocated closer to the front and rear waist members' outer ends 21, 31 than the high elastic zones 83 includes a relatively large area in which none of the front or rear waist elastics 26, 36 is present. Consequentially, the helper's or the user's fingers are smoothly caught by the elastic yarns or threads when the helper or the user grasps the front and rear waist members 20, 30 to put the diaper 1 on the wearer's body. In this way, handling to pull the diaper 1 up or down is facilitated. The unique arrangement such that the crotch member's front and rear ends 41, 42 are attached to the front and rear waist members 20, 30, respectively, at the positions corresponding to the high elastic zones 83 which are allocated closer to the crotch region 4 than the low elastic zones 82 advantageously functions to eliminate the apprehension that the presence of the crotch member 40 might enhance the intrinsic stiffness of the low elastic zones 82 and make it difficult to catch the helper's or user's fingers.

In the respective leg elastic zones 84 of the front and rear waist members 20, 30, the front and rear waist elastics 26, 36 are arranged at a relatively large pitch and therefore the contractile forces thereof are sufficiently low to assure these leg elastic zones 84 to be easily stretched or contracted on the wearer's body in the transverse direction X. The front and rear waist elastics 26, 36 arranged in the leg elastic zones cooperate with the crotch elastics 46 to surround substantially entirely peripheral edges of the leg-openings which are adapted to surround the wearer's groins and to be kept in close contact therewith. Being kept in close contact with the wearer's legs but not excessively tightening the wearer's legs, the peripheral edges of the leg-openings defined in this manner can prevent leakage of body waste, such as urine.

Transversely opposite laterals of the crotch member 40 are folded back along the fold lines 48 in the transverse direction X, the folded regions 49 are bonded to the front and rear waist members 20, 30 and the folded regions 49 are provided with the first and second crotch elastics 46, 47.

With this arrangement, it is possible to put the folded regions 49 and particularly the transversely opposite side edge portions 43 of the crotch member 40 in close contact with the wearer's body. The liquid-absorbent structure 50 is placed between the fold lines 48 spaced from each other in the transverse direction X and thereby the liquid-absorbent structure 50 can be spaced from the wearer's body. In this way, diaper rash due to a direct contact of body waste excreted on the liquid-absorbent structure 50 with the wearer's skin can be prevented and, at the same time, body waste can be prevented from leaking beyond the peripheral edges of the leg-openings.

Referring to FIGS. 1 through 6, the crotch member 40 having been bonded to the front and rear waist members 20, 30 is provided on its garment-facing side with cover sheets 70 so as to cover the crotch member's front and rear ends 41, 42, respectively. Each of the cover sheets 70 may be formed of a fibrous nonwoven fabric or the like having a basis mass of about 10 to about 30 g/m². The cover sheet 70 is contoured by inner and outer ends 71, 72 extending in the transverse direction X and transversely opposite side edges 73 extending in the longitudinal direction Y. The side edges 73 are joined together with inner and outer sheets 24, 25; 34, 35 of the front and rear waist members 20, 30 along the seam arrays 5.

The cover sheets 70, 70 are attached to the crotch member 40 so as to overlap, at least partially, the respective low elastic zones 82. The respective outer ends 71 are placed in the associated waist elastic zones 81 and directly bonded to the outer sheets 25, 35 of the front and rear waist members 20, 30. The respective inner ends 72 are placed in the high elastic zones 83 and bonded at middle areas thereof to the crotch member 40 and at transversely opposite lateral areas extending outward beyond the crotch member 40 in the transverse direction X to the outer sheets 25, 35 of the front and rear waist members 20, 30. In this manner, the cover sheets 70 are bonded to the associated regions with hot melt adhesives (not shown) applied to substantially over the entire areas thereof.

The crotch member 40 attached to the respective garment-facing sides of the front and rear waist members 20, is additionally provided along the front and rear ends 41, 42 thereof with the cover sheets 70, 70 so as to cover these front and rear ends 41, 42. With such arrangement, it is possible to prevent the wearer's limb or garment from being caught by the front and rear ends 41, 42 of the crotch member 40 and causing the crotch member 40 to be peeled off from the front and rear waist members 20, 30. Certainly, there is a possibility that the wearer's foot might be caught by the crotch member 40 and, in consequence, the crotch member 40 might be pulled nearly away from the front and rear waist members 20, 30. However, the crotch member 40 is bonded to the front and rear waist members 20, 30 not only in the first and second bonded regions 61, 62 but also by the intermediary of the cover sheets 70, 70 and therefore the crotch region 40 would be unlikely to be completely peeled off from the front and rear waist members 20, 30. The first and second bonded regions 61, 62 are formed so as to define the non-bonded regions 63 in the central region of the crotch member 40 and a joint strength of the crotch member 40 is necessarily lower than the case in which the non-bonded regions 63 are not left. However, the cover sheets 70 effectively prevent peeling off of the crotch member 40 from the front and rear waist members 20, 30. It may be apprehended that, if the strength of the front and rear waist members 20, 30 is relatively low, these waist members 20, 30 might be torn in the course of pulling the diaper 1 up or down with the helper's or user's fingers caught by the low elastic zones 82 of the front and rear waist members 20, 30. However, the cover sheets 70 provided so as to overlap the respective low elastic zones 82 effectively prevent the front and rear waist members 20, 30 from being torn during the above-mentioned handling of the diaper 1.

The tensile stress values in the transverse direction were measured on the respective elastic zones of the diaper 1 according to the above-mentioned embodiment will be comparatively described hereunder. The measurement was carried out using "INSTRON" manufactured by Shimadzu Corporation in Japan, which is available in Japan. The measurement included the following steps.

A diaper having the same construction as the diaper 1 was cut into the respective elastic zones. Specifically, this diaper was cut in parallel to the front and rear members' outer ends 21, 31 into first zones extending from the front and rear waist members' outer ends 21, 31 to the levels 50 mm spaced inward from the respective outer ends 21, 31 in the longitudinal direction, second zones extending from the above-mentioned 50 mm levels to the levels 75 mm spaced inward from the respective outer ends 21, 31, third zones extending from the above-mentioned 75 mm levels to the levels 140 mm spaced inward from the respective outer ends 21, 31, and fourth zones extending from the above-mentioned 140 mm levels to the levels 170 mm spaced inward from the respective outer ends 21, 31. These first to fourth zones corresponding to the waist elastic zones 81, the low elastic zones 82, the high elastic zones 83 and the leg elastic zones 84, respectively, were designated as samples A, B, C and D. The sample A included five elastic yarns or threads each having fineness of about 940 dtex, the sample B included a single elastic yarn having fineness of about 780 dtex, the sample C included nine elastic yarns or threads each having a fineness of about 940 dtex and sample D included two elastic yarns or threads each having fineness of about 780 dtex. The respective samples included, in addition to the front and rear waist members 20, 30, portions of the crotch member and the cover sheets 70 allocated in the respective zones wherein these components remained joined together along the seam arrays 5 to be maintained in the annular shape. It should be noted here that the above-mentioned method for measurement is also applicable to not only the above-mentioned dimensions of the levels and the fineness, but also dimensions of other levels and finenesses, as will be obvious to these skilled in the art.

A stationary type long jig set consisting of an upper jig and a lower jig was used, wherein the upper jig has a dry scaly skin-like upper side and the lower jig has a dry scaly skin-like lower side. The upper and lower jigs were 180 mm spaced from each other in the vertical direction and the annular sample was fixed by inserting the jig set into the annular sample with one side of the seam arrays lying on the upper side of the upper jig and the opposed side of the seam arrays lying under the lower jig.

The jig set was moved at a rate of 300 mm/min until the chucks (jigs) were spaced 460 mm from each other, whereupon the movement was reversed until the chucks returned to the 180 mm distance, and then the movement was reversed again until the chucks were spaced 460 mm from each other. The tensile stress at this moment is measured.

The measurement results indicated that the tensile stress values of the samples A through D were 2.5N, 0.9N, 3.5N and 1.8N, respectively, and represented by a relationship of C>A>D>B.

Accordingly, it was found that the tensile stress of the diaper 1 in the transverse direction can be represented by the relationship of the high elastic zones 83>the waist elastic zones 81>the leg elastic zones 84>the low elastic zones 82. With the diaper 1 being put on the wearer's body, the high elastic zones 83 correspond to the wearer's ilium. In other words, the diaper 1 exhibits a relatively high tensile stress in its region corresponding to the vicinity of the wearer's ilium, and a relatively low tensile stress in the vicinity of the waist-opening. With the construction as described above, the diaper 1 according to one or more embodiments of the present invention can provide a comfortable feeling to the wearer.

The respective dimensions of the waist elastic zones, the low elastic zones, the high elastic zones and the leg elastic zones are not limited to those exemplarily described above and may be appropriately selected. So far as the high elastic zones 83 fall on the wearer's ilium and/or the crotch member are joined to the front and rear waist elastic members in the high elastic zones 83, diapers in accordance with further embodiments of the present invention may be implemented without one or more of the remaining elastic zones. While the diaper 1 is symmetrically shaped in the longitudinal direction, the locations at which the crotch member is joined to the front and rear waist regions as well as the dimensions of the respective elastic zones may be different between the front waist region and the rear waist region. Furthermore, diapers in accordance with further embodiments of the present invention may be implemented, including none of the cover sheets.

The number of the front and rear waist elastics 26, 36 to be attached to the front and rear waist members 20, 30 as well as the pitch at which the elastics are arranged in each of the elastic zones may be appropriately selected. These parameters may be different, if desired, between the front waist region and the rear waist region. While elastic yarns or threads are used as the front and rear waist elastics 26, 36 for the diaper 1 according to the aforementioned embodiment, it is also possible to use, for example, belt-like or sheet-like elastics as the elastics according to further embodiments of the present invention.

The component members of the diaper 1 are not limited to those described in this specification but the other various types of material widely used in the relevant technical field may be used without limitation. The terms "first" and "second" used in the specification and claims of the present application are used merely to distinguish similar elements, similar positions or similar means.

The embodiments described above may be arranged in at least the following items:

A disposable wearing article has a longitudinal direction and a transverse direction, and including a body-facing side, a garment-facing side, a front waist region defined by a front waist member, a rear waist region defined by a rear waist member and a crotch region defined by a crotch member and extending in the longitudinal direction between the front waist region and the rear waist region. The front and rear waist members are respectively provided with a plurality of waist elastics extending in the transverse direction and spaced one from another in the longitudinal direction and the waist elastics are bonded under tension and in a contractible manner to the front and rear waist members.

The article further includes:

the crotch member has front and rear ends which extend in the transverse direction and along which the crotch member is bonded to respective the garment-facing sides of the front and rear waist members in first bonded regions extending in the transverse direction; at least one of the front and rear waist members has a plurality of elastic zones defined in the longitudinal direction and having different tensile stresses in the transverse direction; and the first bonded regions are formed in associated high elastic zones included in the plurality of elastic zones and having the highest tensile stress.

Additionally, one or more of the following embodiments may be provided.

(i) The front waist member and the rear waist member have a pair of transversely opposite front waist side edges and a pair of transversely opposite rear waist side edges, respectively, and the waist elastics continuously extend between the front waist side edges and between the rear waist side edges, respectively.

(ii) The crotch member is bonded to the garment-facing sides of the front waist member and the rear waist member also in second bonded regions defined outboard of the first bonded regions as viewed in the transverse direction and extending toward the crotch region in the longitudinal direction, and non-bonded regions defined by the first bonded regions and the second bonded regions lie substantially in the middle between the second bonded regions as viewed in the transverse direction and open toward the crotch region.

(iii) The high elastic zones are adapted to be allocated on the wearer's ilium when the article is put on the wearer's body.

(iv) The plurality of elastic zones further include waist elastic zones each having the tensile stress in the transverse direction lower than that of the high elastic zones and positioned outside from the high elastic zones as viewed in the longitudinal direction.

(v) The plurality of elastic zones further include waist elastic zones each having the tensile stress in the transverse direction lower than that of the high elastic zones and positioned outside from the high elastic zones as viewed in the longitudinal direction.

(vi) The plurality of elastic zones further include leg elastic zones each having the tensile stress in the transverse direction lower than that of the waist elastic zones and positioned inward from the high elastic zones as viewed in the longitudinal direction.

(vii) The plurality of elastic zones further include low elastic zones having the tensile stress in the transverse direction lower than that of the waist elastic zones and positioned between the high elastic zones and the waist elastic zones.

(viii) The plurality of elastic zones further include low elastic zones having the tensile stress in the transverse direction lower than that of the waist elastic zones and positioned between the high elastic zones and the waist elastic zones.

(ix) The crotch member includes crotch elastics attached thereto so as to extend along transversely opposite side edges thereof.

(x) Transversely opposite side edge portions of the crotch member are folded inward in the transverse direction along fold lines extending in the longitudinal direction so that regions folded in this manner face the front waist member and the rear waist member, respectively, and the second bonded regions positionally correspond to these folded regions.

(xi) A liquid-absorbent structure contoured by front and rear ends and transversely opposite side edges is placed on the garment-facing side of the crotch member so that the front and rear ends of the liquid-absorbent structure are respectively positioned between the crotch member's front and rear ends as viewed in the longitudinal direction and the transversely opposite side edges of the liquid-absorbent structure are respectively positioned between the fold lines as viewed in the transverse direction.

(xii) The pair of front waist side edges and the pair of rear waist side edges are respectively joined together to maintain the front and rear waist members in an annular shape.

(xiii) There are provided cover sheets bonded to the garment-facing side of the crotch member so that the cover sheets cover the crotch member's front and rear ends and at least partially overlap the low elastic zones.

(xiv) There are provided cover sheets bonded to the garment-facing side of the crotch member so that the cover sheets cover the crotch member's front and rear ends and at least partially overlap low elastic zones included in the plurality of elastic zones and having the lowest tensile stress.

(xv) The cover sheets have, in the longitudinal direction, outer ends and inner ends; and the inner ends of the cover sheets are placed in the high elastic zones.

(xvi) The plurality of elastic zones further include waist elastic zones each having the tensile stress in the transverse direction lower than that of the high elastic zones and higher than that of the low elastic zones; the low elastic zones are positioned between the high elastic zones and the waist elastic zones; and the outer ends of the cover sheets are placed in the waist elastic zones.

This application claims the benefit of Japanese Application No. 2010-195117 the entire disclosure of which is incorporated by reference herein.

REFERENCE SIGNS LIST 1 diaper (disposable wearing article)
2 front waist region
3 rear waist region
4 crotch region
20 front waist member
23 front waist side edges
30 rear waist member
33 rear waist side edges
26 front waist elastics (waist elastics)
36 rear waist elastics (waist elastics)
40 crotch member
41 crotch member's front end
42 crotch member's rear end
43 crotch member's side edge portions
46 first crotch elastics
47 second crotch elastics
48 fold lines
50 liquid-absorbent structure
51 liquid-absorbent structure's front end
52 liquid-absorbent structure's rear end
53 liquid-absorbent structure's side edges
61 first bonded regions
63 second bonded regions
63 non-bonded regions
70 cover sheet
71 cover sheet's outer end
72 cover sheet's inner end
81 waist elastic zones
82 low elastic zones
83 high elastic zones
84 leg elastic zones
X transverse direction
Y longitudinal direction

The invention claimed is:

1. A disposable wearing article having a longitudinal direction and a transverse direction, the disposable wearing article comprising:
a body-facing side for facing a wearer's body,
a garment-facing side for facing away from the wearer's body,
a front waist region defined by a front waist member,
a rear waist region defined by a rear waist member, and
a crotch region defined by a crotch member and extending in the longitudinal direction between the front waist region and the rear waist region,
wherein
the front and rear waist members are respectively provided with a plurality of waist elastics extending in the transverse direction and spaced one from another in the longitudinal direction and the waist elastics are bonded under tension and in a contractible manner to the front and rear waist members;
the crotch member has front and rear ends which extend in the transverse direction and along which the crotch member is bonded to the garment-facing sides of the front and rear waist members, respectively, in first bonded regions extending in the transverse direction;
at least one of the front and rear waist members has a plurality of elastic zones defined in the longitudinal direction and having different tensile stresses in the transverse direction; and
the first bonded regions are formed in associated high elastic zones included in the plurality of elastic zones and having the highest tensile stress.

2. The disposable wearing article defined by claim 1, wherein the front waist member and the rear waist member have a pair of transversely opposite front waist side edges and a pair of transversely opposite rear waist side edges, respectively, and the waist elastics continuously extend between the front waist side edges and between the rear waist side edges, respectively.

3. The disposable wearing article defined by claim 2, wherein the pair of front waist side edges and the pair of rear waist side edges are respectively joined together to maintain the front and rear waist members in an annular shape.

4. The disposable wearing article defined by claim 1, wherein
the crotch member is bonded to the garment-facing sides of the front waist member and the rear waist member also in second bonded regions defined outboard of the first bonded regions as viewed in the transverse direction and extending toward the crotch region in the longitudinal direction, and
non-bonded regions defined by the first bonded regions and the second bonded regions lie substantially in the middle between the second bonded regions as viewed in the transverse direction and open toward the crotch region.

5. The disposable wearing article defined by claim 4, wherein the crotch member includes crotch elastics attached thereto so as to extend along transversely opposite side edges thereof.

6. The disposable wearing article defined by claim 4, wherein transversely opposite side edge portions of the crotch member are folded inward in the transverse direction along fold lines extending in the longitudinal direction so that regions folded in this manner face the front waist member and the rear waist member, respectively, and the second bonded regions positionally correspond to these folded regions.

7. The disposable wearing article defined by claim 6, wherein a liquid-absorbent structure contoured by front and rear ends and transversely opposite side edges is placed on the garment-facing side of the crotch member so that the front and rear ends of the liquid-absorbent structure are respectively positioned between the crotch member's front and rear ends as viewed in the longitudinal direction and the transversely opposite side edges of the liquid-absorbent structure are respectively positioned between the fold lines as viewed in the transverse direction.

8. The disposable wearing article defined by claim 1, wherein the high elastic zones are adapted to be allocated on the wearer's ilium when the article is put on the wearer's body.

9. The disposable wearing article defined by claim 1, wherein the plurality of elastic zones further include waist elastic zones each having the tensile stress in the transverse direction lower than that of the high elastic zones and positioned outside from the high elastic zones as viewed in the longitudinal direction.

10. The disposable wearing article defined by claim 9, wherein the plurality of elastic zones further include leg elastic zones each having the tensile stress in the transverse direction lower than that of the waist elastic zones and positioned inward from the high elastic zones as viewed in the longitudinal direction.

11. The disposable wearing article defined by claim 10, wherein the plurality of elastic zones further include low elastic zones each having the tensile stress in the transverse direction lower than that of the leg elastic zones and positioned between the high elastic zones and the waist elastic zones.

12. The disposable wearing article defined by claim 9, wherein the plurality of elastic zones further include low elastic zones having the tensile stress in the transverse direction lower than that of the waist elastic zones and positioned between the high elastic zones and the waist elastic zones.

13. The disposable wearing article defined by claim 12, further comprising cover sheets bonded to the garment-facing side of the crotch member so that the cover sheets cover the crotch member's front and rear ends and at least partially overlap the low elastic zones.

14. The disposable wearing article defined by claim 1, wherein the plurality of elastic zones further include leg elastic zones each having the tensile stress in the transverse direction lower than that of the high elastic zones and positioned inward from the high elastic zones as viewed in the longitudinal direction.

15. The disposable wearing article defined by claim 1, further comprising cover sheets bonded to the garment-facing side of the crotch member so that the cover sheets cover the crotch member's front and rear ends and at least partially overlap low elastic zones included in the plurality of elastic zones and having the lowest tensile stress.

16. The disposable wearing article defined by claim 15, wherein
 the cover sheets have, in the longitudinal direction, outer ends and inner ends; and
 the inner ends of the cover sheets are placed in the high elastic zones.

17. The disposable wearing article defined by claim 1, further comprising cover sheets bonded to the garment-facing side of the crotch member so that the cover sheets cover the crotch member's front and rear ends, wherein
 the plurality of elastic zones further include waist elastic zones each having the tensile stress in the transverse direction lower than that of the high elastic zones and higher than that of low elastic zones among the plurality of elastic zones;
 the low elastic zones are positioned between the high elastic zones and the waist elastic zones; and
 the outer ends of the cover sheets are placed in the waist elastic zones.

* * * * *